US008915962B1

(12) United States Patent
Suddaby

(10) Patent No.: US 8,915,962 B1
(45) Date of Patent: *Dec. 23, 2014

(54) FACET JOINT FIXATION DEVICE

(76) Inventor: Loubert S. Suddaby, Orchard Park, NY (US)

( * ) Notice: Subject to any disclaimer, the term of this patent is extended or adjusted under 35 U.S.C. 154(b) by 329 days.

This patent is subject to a terminal disclaimer.

(21) Appl. No.: 13/329,786

(22) Filed: Dec. 19, 2011

Related U.S. Application Data

(63) Continuation-in-part of application No. 12/148,986, filed on Apr. 24, 2008, now Pat. No. 8,080,046.

(51) Int. Cl.
*A61F 2/44* (2006.01)

(52) U.S. Cl.
USPC ..................................... 623/17.11

(58) Field of Classification Search
USPC .......................... 623/17.11–17.19
See application file for complete search history.

(56) References Cited

U.S. PATENT DOCUMENTS

| 4,401,112 | A  | 8/1983  | Rezaian         |
|-----------|----|---------|-----------------|
| 5,015,247 | A  | 5/1991  | Michelson       |
| 5,496,318 | A  | 3/1996  | Howland et al.  |
| 5,645,599 | A  | 7/1997  | Samani          |
| 5,772,661 | A  | 6/1998  | Michelson       |
| 5,840,078 | A  | 11/1998 | Yerys           |
| 6,001,130 | A  | 12/1999 | Bryan et al.    |
| 6,156,037 | A  | 12/2000 | LeHuec et al.   |
| 6,235,059 | B1 | 5/2001  | Benezech et al. |
| 6,770,096 | B2 | 8/2004  | Bolger et al.   |
| 6,923,810 | B1 | 8/2005  | Michelson       |
| 6,972,035 | B2 | 12/2005 | Michelson       |
| 7,135,024 | B2 | 11/2006 | Cook et al.     |
| 7,201,751 | B2 | 4/2007  | Zucherman et al.|
| 8,080,046 | B2* | 12/2011 | Suddaby ................. 606/324 |
| 2004/0006343 | A1 | 1/2004 | Sevrain |
| 2004/0073214 | A1 | 4/2004 | Mehdizadeh |
| 2004/0087948 | A1 | 5/2004 | Suddaby |
| 2004/0143280 | A1 | 7/2004 | Suddaby |
| 2005/0267480 | A1 | 12/2005 | Suddaby |
| 2006/0271080 | A1 | 11/2006 | Suddaby |
| 2007/0179500 | A1 | 8/2007 | Chin et al. |
| 2007/0225740 | A1 | 9/2007 | Suddaby |
| 2009/0043394 | A1* | 2/2009 | Zdeblick et al. ........... 623/17.16 |
| 2009/0164016 | A1* | 6/2009 | Georgy et al. ............ 623/17.11 |
| 2009/0254181 | A1* | 10/2009 | Boyd et al. .............. 623/17.11 |
| 2010/0198272 | A1* | 8/2010 | Keyer et al. ............. 606/302 |
| 2010/0211176 | A1* | 8/2010 | Greenhalgh ............. 623/17.15 |
| 2010/0312346 | A1* | 12/2010 | Kueenzi et al. ........... 623/17.16 |

\* cited by examiner

*Primary Examiner* — Suzette J Gherbi
(74) *Attorney, Agent, or Firm* — Simpson & Simpson, PLLC

(57) ABSTRACT

A device for fixing the positions of proximate bone elements including an inter-bone implant adapted to be implanted between suitably prepared proximate bone elements, the inter-bone implant having an internally threaded aperture, a bone fixation apparatus including a base having an eyelet and a means connected to the base for mechanically fixing the positions of the proximate bone elements relative to each other, the eyelet being substantially aligned with the internally threaded aperture, and a screw having a head and a threaded shaft extending therefrom, wherein the shaft is operatively arranged to extend through the eyelet and threadingly engage the internally threaded aperture, and the screw is operatively arranged to secure the bone fixation apparatus to the inter-bone implant.

6 Claims, 18 Drawing Sheets

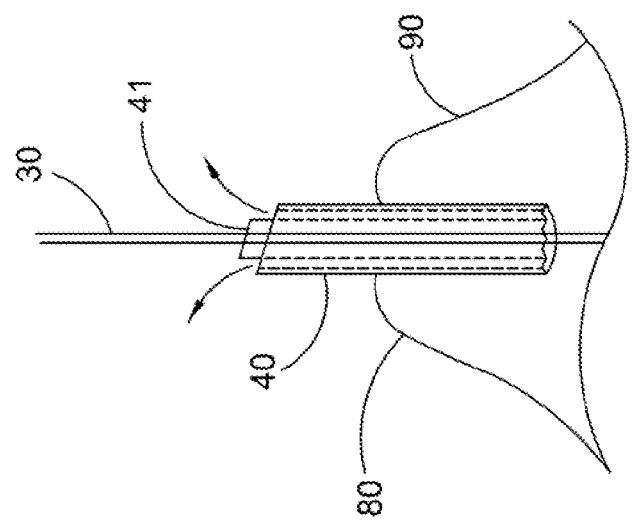
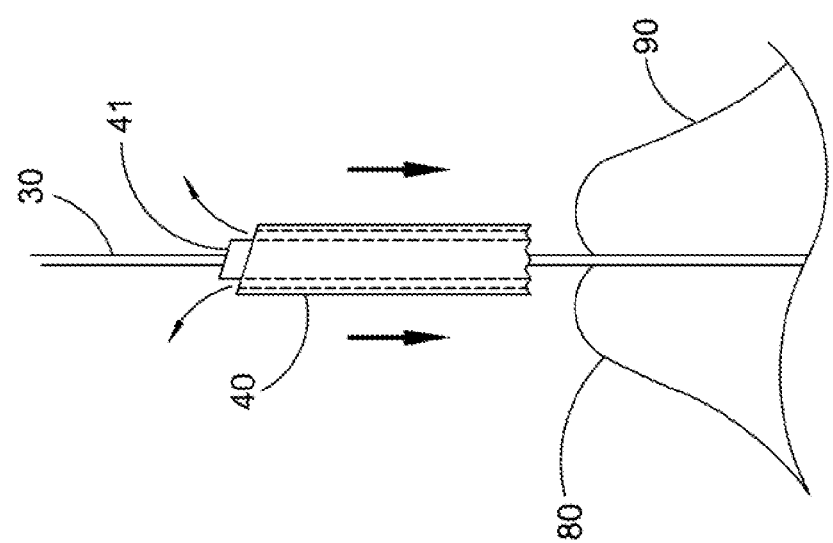
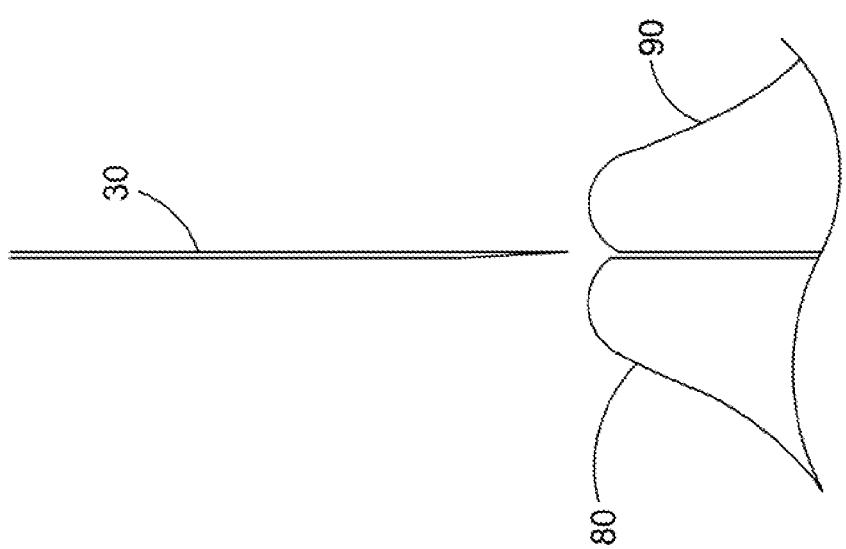

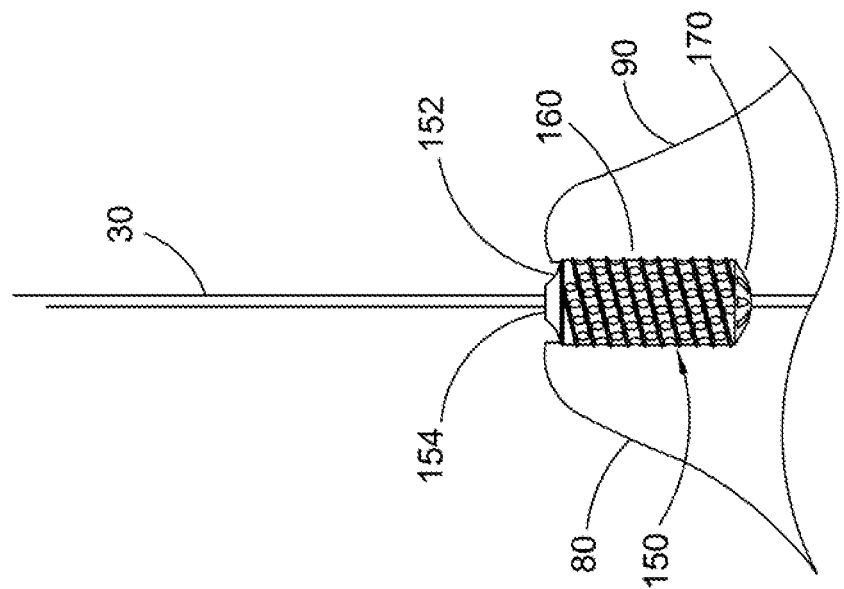
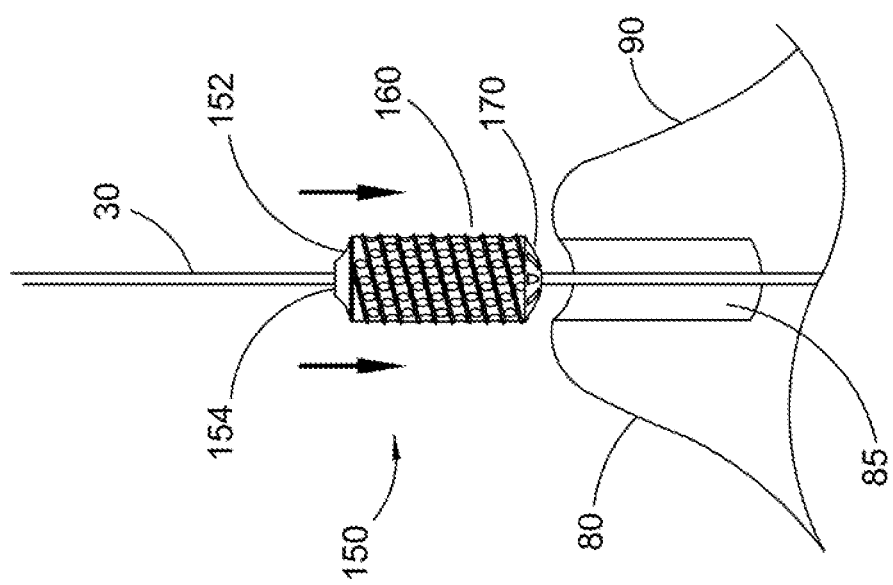

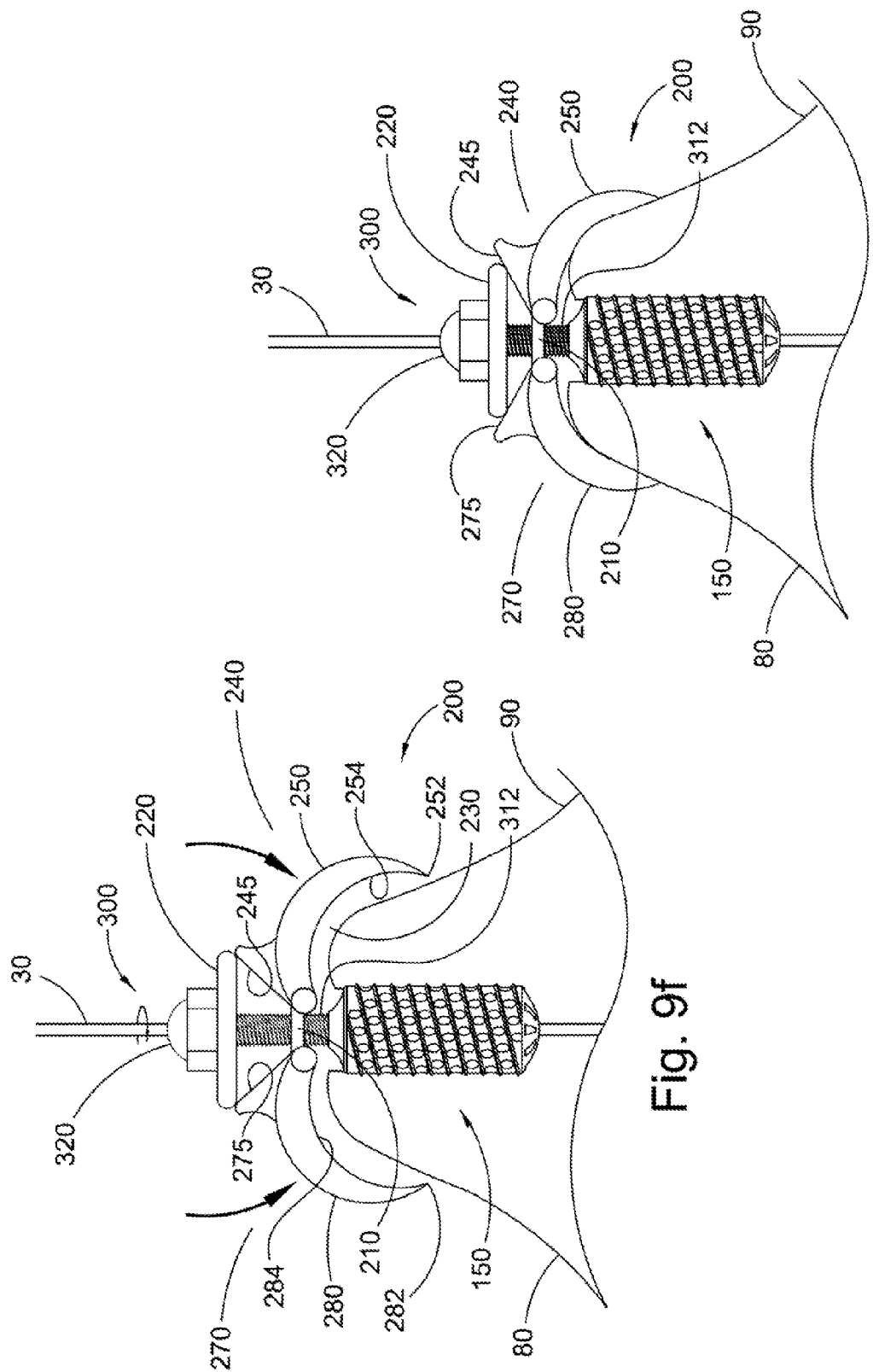

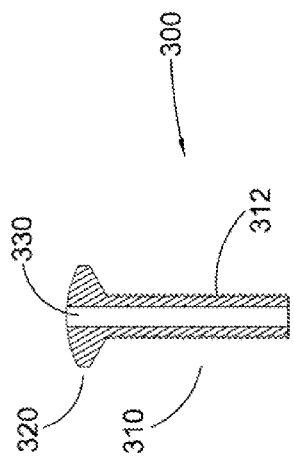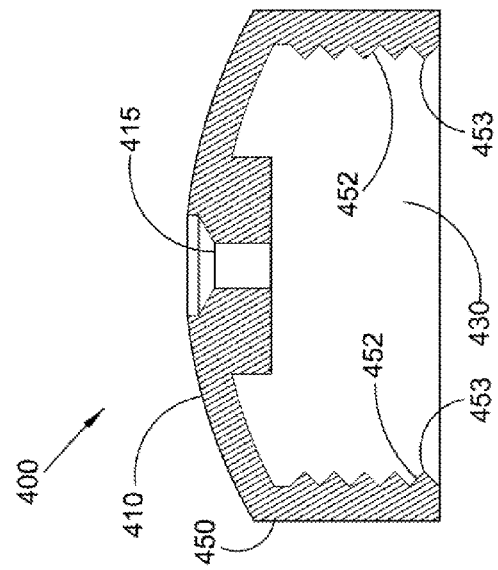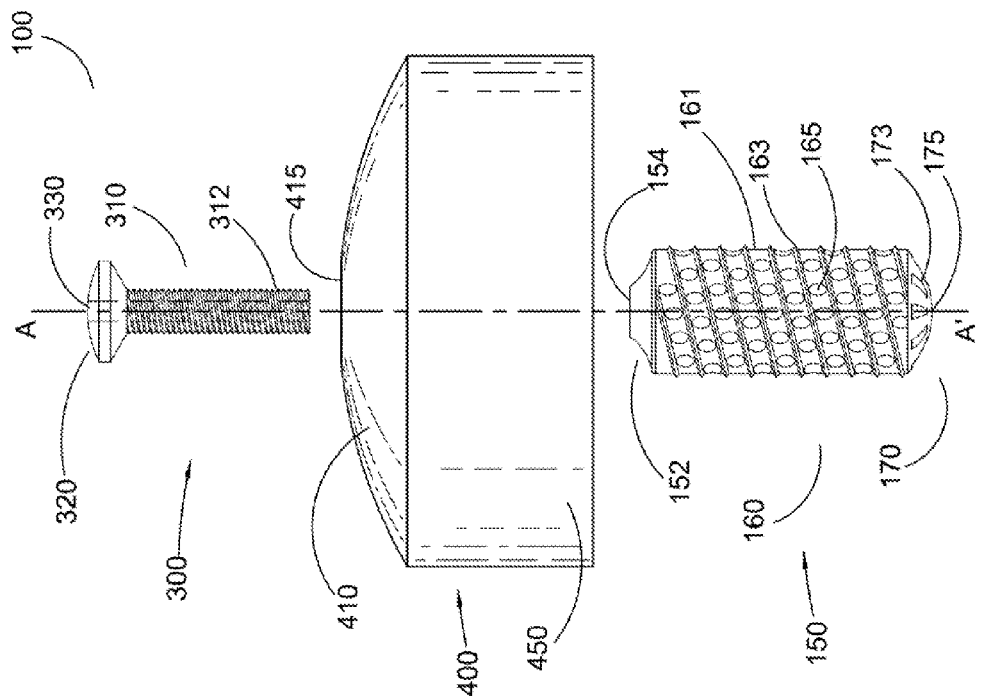

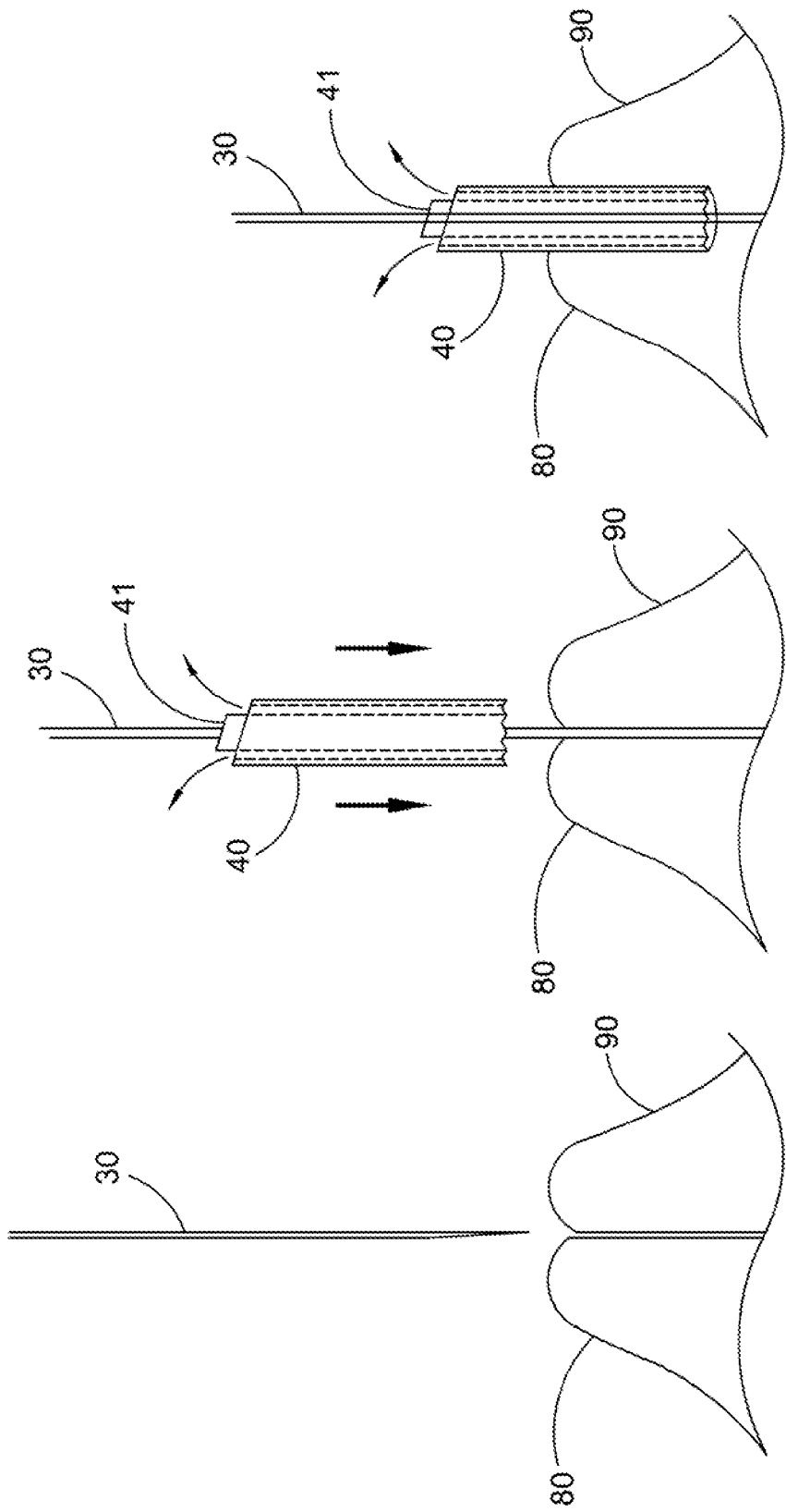

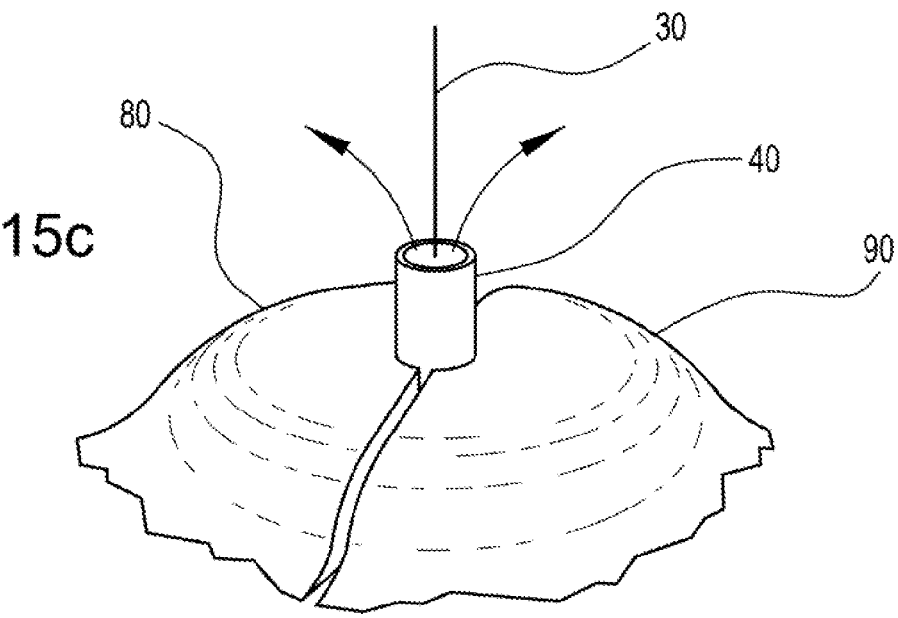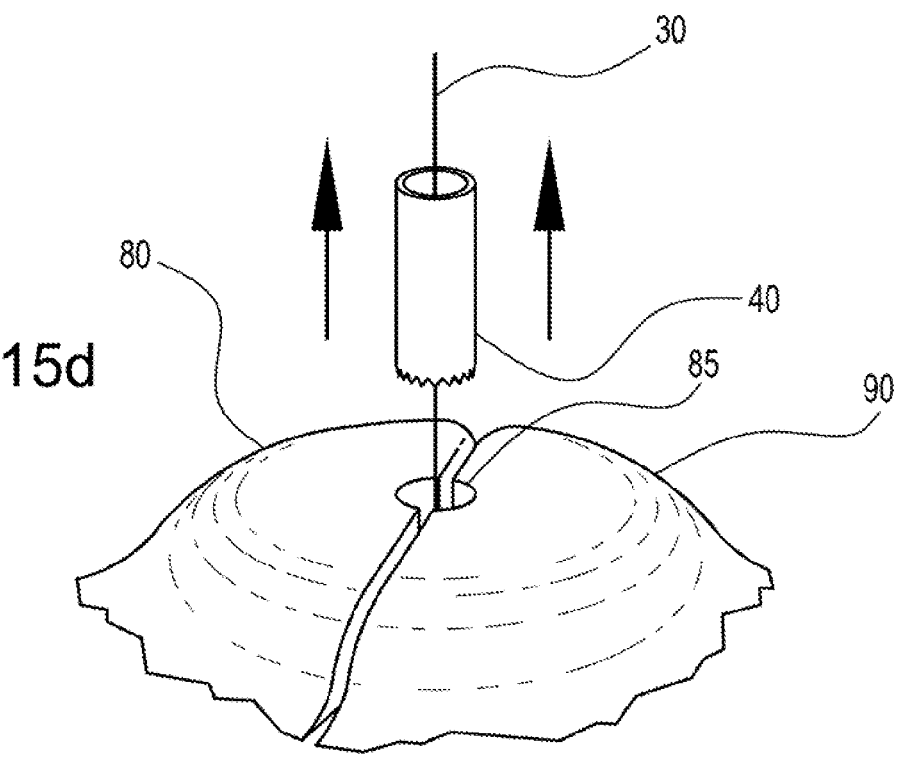

FACET JOINT FIXATION DEVICE

CROSS REFERENCE TO RELATED APPLICATIONS

This application is filed under 35 U.S.C. §120 as a continuation-in-part patent application of U.S. patent application Ser. No. 12/148,986, now U.S. Pat. No. 8,080,046, filed Apr. 24, 2008, which application is incorporated herein by reference in its entirety.

FIELD OF THE INVENTION

This invention relates to the field of orthopedic surgery and, particularly, to inter-bone fixation and fusion devices and, even more particularly, to interarticular facet joint fixation and fusion devices.

BACKGROUND OF THE INVENTION

The intervertebral discs of the human spine are prone to degeneration. In particular, the intervertebral discs located in highly mobile regions of the spine are disproportionately prone to degeneration, primarily due to overt and covert trauma to the tissue that occurs in the course of repetitive activities. Such trauma tends to disrupt the internal architecture of the disc and leads to bulging, herniation or protrusion of pieces of the disc, and the eventual collapse of the disc space. The resultant mechanical and/or chemical irritation of the surrounding neural elements, such as the spinal cord and nerves, may cause pain, inflammation and varying degrees of osteoarthritis and disability. Additionally, the loss of disc space height relaxes tension on the longitudinal spinal ligaments, thereby contributing to varying degrees of spinal instability.

Various treatments have been developed to treat such intervertebral disc degeneration. Many of these treatments involve the fusion of adjacent vertebra in order to limit their ability to move independently from each other, as such independent movement tends to exacerbate the degeneration of the interposed disc. These prior spinal fusion operations often involve either the passive grafting of bone between the surfaces of proximate articular processes in a facet joint that is denuded of synovium, or they involve the mechanical fixation of the facet joint with a simple screw.

These prior treatments, while fairly adequate for their purpose, suffer from a number of drawbacks. For example, operations that involve the passive grafting of bone require additional instrumented fixation of the spine to prevent dislodgement of the bone grafts from between the articular surfaces of the joint. Operations involving the mechanical fixation with a simple screw are largely adjunctive, that is, the screw alone is not sufficient as a means for fixing the facet joint. The long term success of this procedure is usually dependent upon bony union occurring elsewhere between the adjacent vertebral elements being fused, i.e., interbody or inter-transverse postero-lateral fusions.

Thus, there is a longfelt need for a facet fixation device that can be utilized either directly in a stand alone facet fusion procedure or as an adjunctive fixator to be utilized when other forms of spinal fusion are employed, e.g., as back up for an anterior fusion. There is also a longfelt need for such a device that may be deployed radiographically or through endoscopically-assisted minimally invasive approaches.

BRIEF SUMMARY OF THE INVENTION

The present invention is a device for fixing the positions of proximate bone elements, which is particularly adapted for the fixation of proximate articular processes in a facet joint (hereinafter referred to as the "facet fixation device" or, simply, the "device"). The device broadly comprises: an inter-bone implant adapted to be implanted between suitably prepared proximate bone elements, the inter-bone implant comprising an internally threaded aperture; a bone fixation apparatus comprising a base having an eyelet and a means connected to the base for mechanically fixing the positions of the proximate bone elements relative to each other, the eyelet being substantially aligned with the internally threaded aperture; and, a screw comprising a head and a threaded shaft extending therefrom, wherein the shaft is operatively arranged to extend through the eyelet and threadingly engage the internally threaded aperture, and the screw is operatively arranged to secure the bone fixation apparatus to the inter-bone implant.

The means for mechanically fixing the positions of the proximate bone elements relative to each other generally comprises substantially opposed surfaces, between which at least a portion of each of the proximate bone elements is immovably secured. The substantially opposed surfaces may be provided by an integral form, such as the inner annular surface of an annular wall, or by separate structures, such as the inner surfaces of opposed jaws.

In an alternate embodiment, the bone fixation device includes a cap that is placed within a recess common to both of the proximate bones. In this embodiment, holes in the cap are aligned with pilot holes within the common recess that are drilled into each of the proximate bones. Screws are inserted through the cap holes into the pilot holes. In this embodiment, the cap fixes the proximate bones by acting as a bridge holding the bones together until the bones grow together through the implant.

It is a general object of the present invention to provide a facet fixation device that can be utilized either directly in a stand alone facet fusion procedure or as an adjunctive fixator to be utilized when other forms of spinal fusion are employed, e.g., as back up for an anterior fusion. It is also the object of this invention to provide for deployment of the device either radiographically or through endoscopically assisted minimally invasive approaches.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which:

FIG. 9a is a side view showing a first step in the implementation of the first embodiment facet fixation device;

FIG. 9b is a side view showing a second step in the implementation of the first embodiment facet fixation device;

FIG. 9c is a side view showing a third step in the implementation of the first embodiment facet fixation device;

FIG. 9d is a side view showing a fourth step in the implementation of the first embodiment facet fixation device;

FIG. 9e is a side view showing a fifth step in the implementation of the first embodiment facet fixation device;

FIG. 9f is a side view showing a sixth step in the implementation of the first embodiment facet fixation device;

FIG. 9g is a side view showing a seventh step in the implementation of the first embodiment facet fixation device;

FIG. 11 is an exploded, side elevational view of the second embodiment facet fixation device;

FIG. 12 is a cross-sectional view taken generally along line 12-12 in FIG. 10;

FIG. 13 is a cross-sectional view taken generally along line 13-13 in FIG. 10;

FIG. 14a is a side view showing a first step in the implementation of the second embodiment facet fixation device;

FIG. 14b is a side view showing a second step in the implementation of the second embodiment facet fixation device;

FIG. 14c is a side view showing a third step in the implementation of the second embodiment facet fixation device;

DETAILED DESCRIPTION OF THE INVENTION

Figure 1:
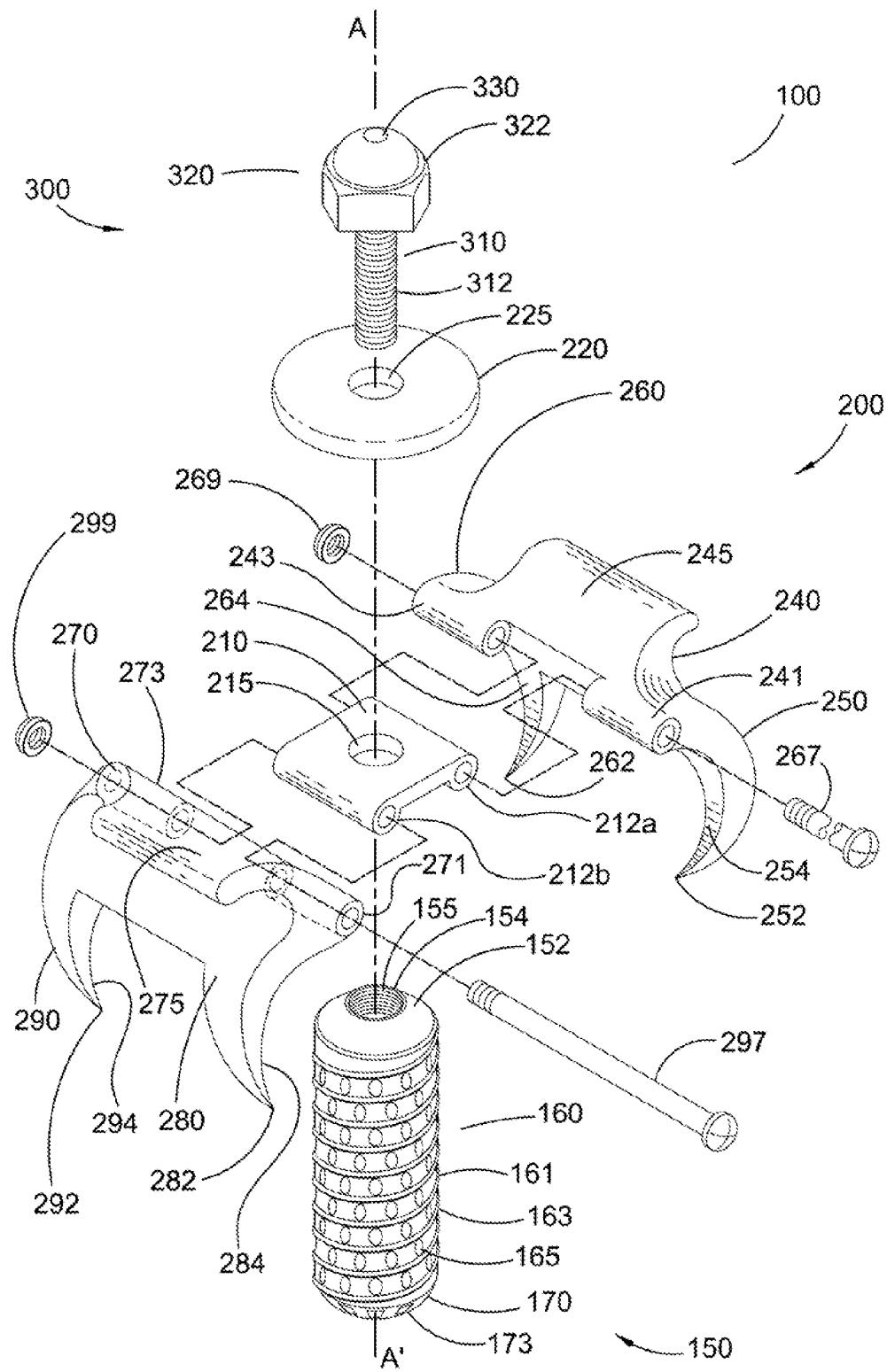
FIG. 1 is an exploded perspective view of a first embodiment of the present invention facet fixation device.
Figure 2:
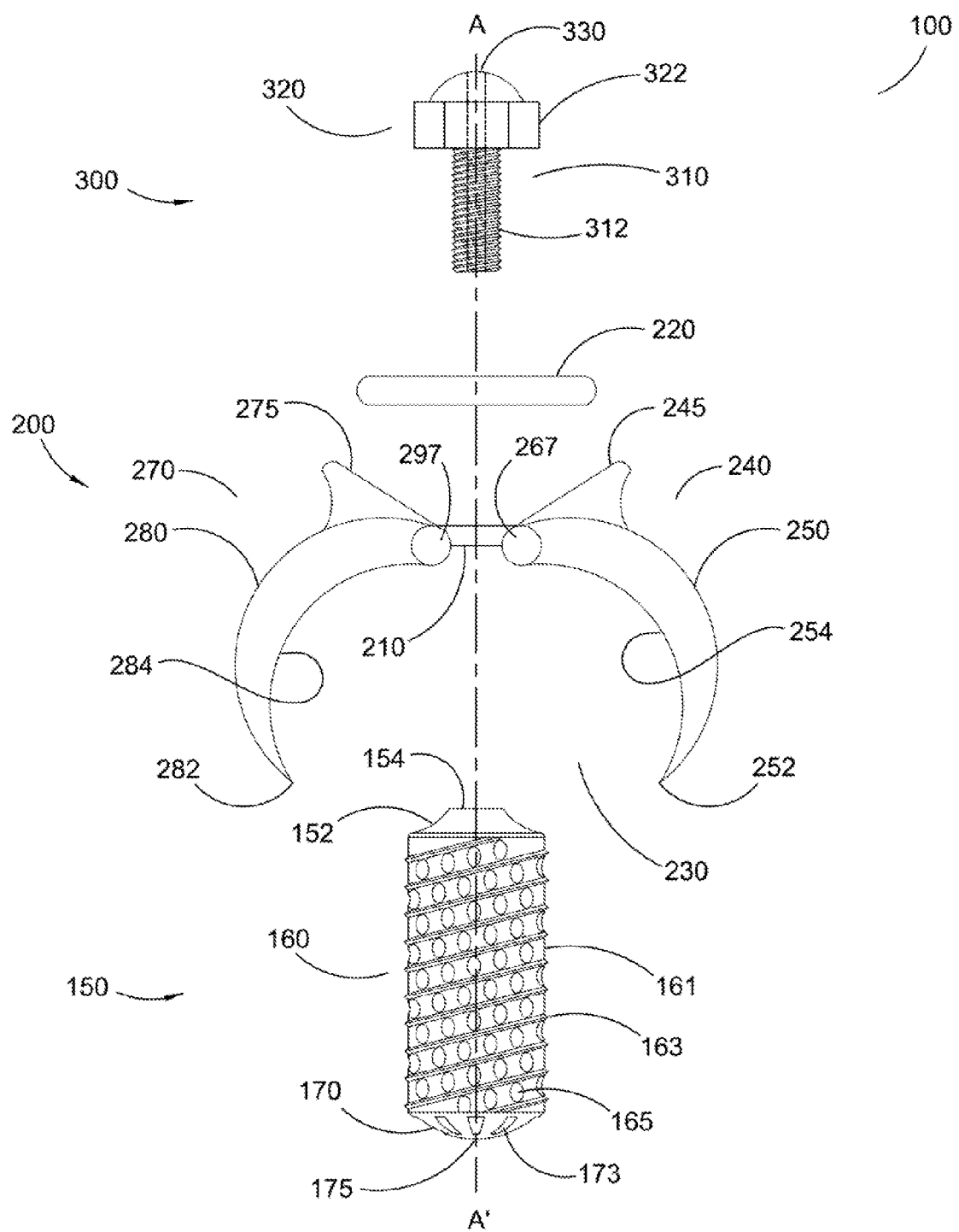
FIG. 2 is an exploded, side elevational view of a first embodiment facet fixation device.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it should be understood that this invention is not limited to the particular methodology, materials and modifications described and as such may, of course, vary. It should also be understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

As stated supra, the present invention device broadly comprises: an inter-bone implant adapted to be implanted between suitably prepared proximate bone elements, the implant having a threaded aperture; a bone fixation apparatus adapted to mechanically fix the position of the proximate bone elements relative to each other and to the inter-bone implant, the bone fixation apparatus including a base having an eyelet substantially aligned with the internally threaded aperture; and, a screw comprising a head and a threaded shaft extending therefrom, the shaft being arranged through the eyelet and threadingly engaged in the internally threaded aperture, and the screw is operatively arranged to fixedly secure the bone fixation apparatus to the inter-bone implant.

The inter-bone implant is operatively arranged to promote the fusion or bony union of the proximate bone elements, and the bone fixation apparatus is operatively arranged to fix the respective position of the proximate bone elements relative to each other and, possibly to the implant, in order to enhance the efficacy of the inter-bone implant. It should be noted that the bone fixation apparatus is not merely supplementary to the inter-bone implant, but is operatively arranged to independently fix the positions of the proximate bone element relative to each other, which may be advantageous in situations where an inter-bone implant is not necessary, not feasible, or simply unwanted due to the nature of the treatment.

Multiple embodiments of the bone fixation apparatus have been contemplated, two of which are shown and described in detail herein. Regardless of the particular embodiment, the bone fixation apparatus comprises a base and a means connected thereto for mechanically fixing the positions of the proximate bone elements relative to each other and, when applicable, to the inter-bone implant. When used in conjunction with the inter-bone implant, the base is preferably in the form of an arcuate or planar plate which includes an eyelet. The eyelet is arranged to receive the shaft of the screw therethrough and allow at least portion of the shaft to reach and threadingly engage the internally threaded aperture of the inter-bone implant.

The means for mechanically fixing the positions of the proximate bone elements relative to each other generally comprises at least two substantially opposed surfaces, between which at least a portion of each of the proximate bone elements is immovably secured. The substantially opposed surfaces may be provided by an integral form, such as the inner annular surface of an annular wall, or by separate structures, such as the inner surfaces of opposed jaws.

The following provides a detailed description of two embodiments of the present invention, which are differentiated from each other primarily by the particular bone fixation apparatus employed. The first embodiment bone fixation apparatus comprises a plurality of opposed jaws, which are operatively arranged to provide the at least two substantially opposed surfaces. The second embodiment bone fixation apparatus comprises an annular wall having an inner annular surface, which is operatively arranged to provide the at least two substantially opposed surfaces.

The first embodiment facet fixation device 100 is best understood in view of FIGS. 1-9g. FIG. 1 is a perspective view of facet fixation device 100 broadly comprising inter-bone implant 150, screw 300, and bone fixation apparatus 200, hereinafter referred to as clamp 200.

Screw 300, which may be any suitable screw, broadly includes head 320, shaft 310 having threads 312, and, preferably, through-bore 330. The screw drive of screw 300 may be of any type, but is preferably hex cap screw 322 when used in combination with clamp 200. Screw 300 may further include plate 220, the function of which is described in detail infra. Plate 220 may be a separate component, as shown in the figures, or integrally formed with head 320.

Figure 3:
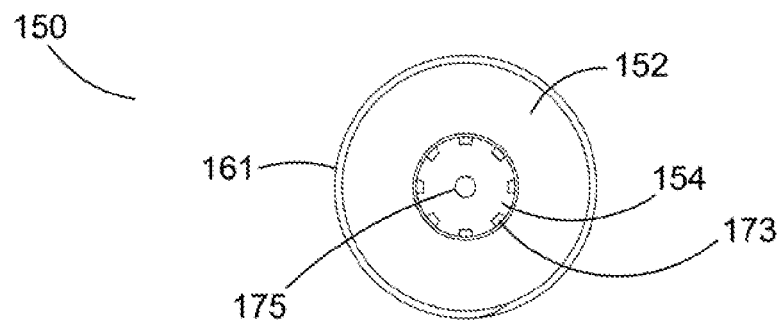
FIG. 3 is a top plan view of an inter-bone implant of the facet fixation device.
Figure 4:
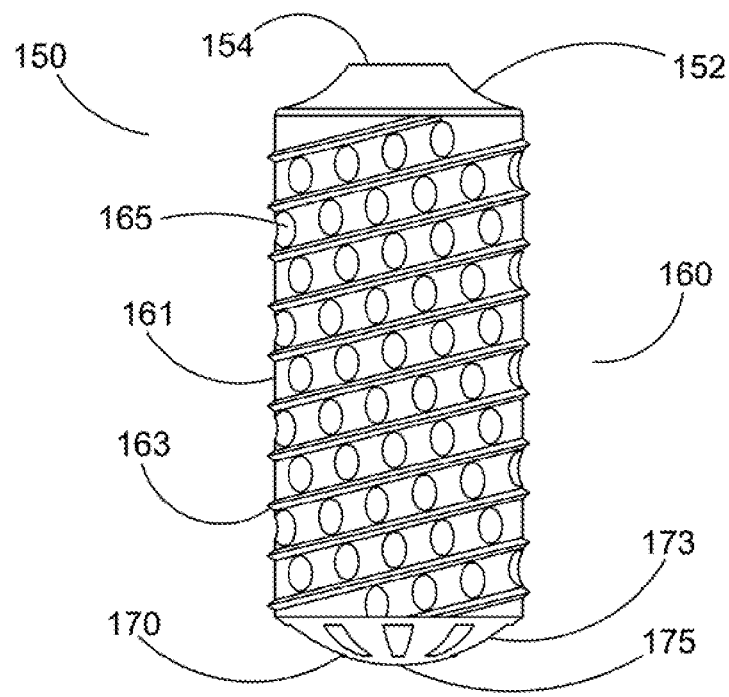
FIG. 4 is a side elevational view of the inter-bone implant.
Figure 5:
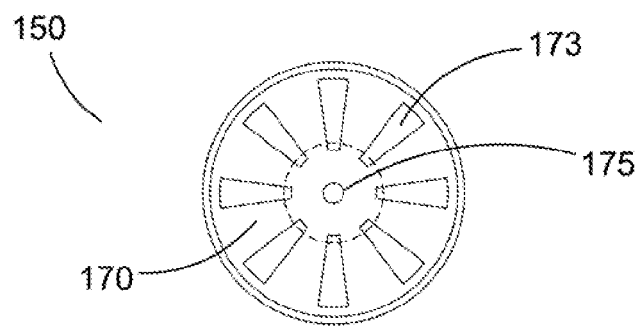
FIG. 5 is a bottom plan view of the inter-bone implant.
Figure 6:
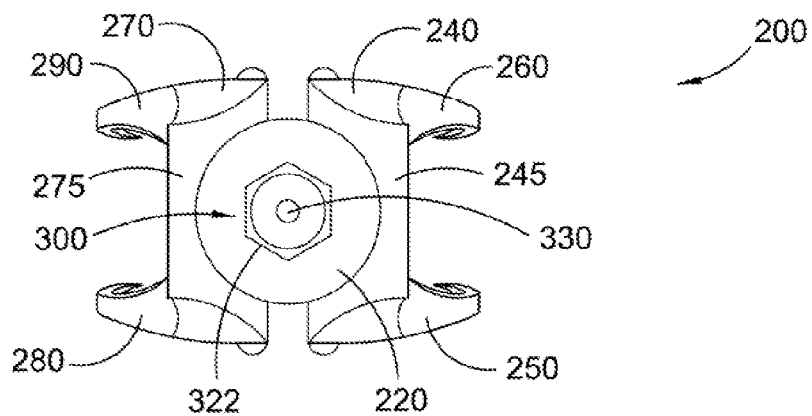
FIG. 6 is a top plan view of the first embodiment bone fixation apparatus.
Figure 7:
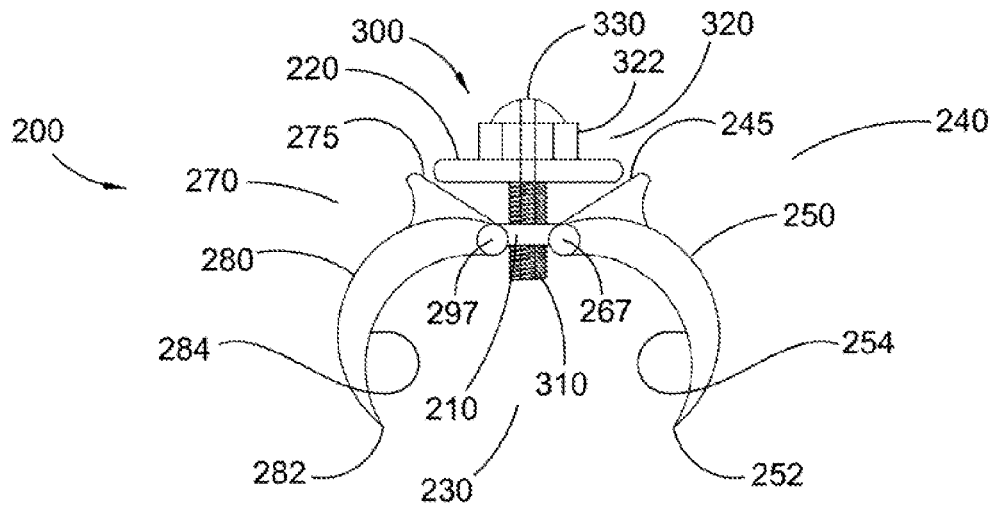
FIG. 7 is a side elevational view of the first embodiment bone fixation apparatus.

As shown in FIGS. 3-5, inter-bone implant 150 comprises body 160, which is preferably hollow and either cylindrical or frustoconical, first end 152, and second end 170. First end 152 includes aperture 154 having internal threads 155, which are operatively arranged to threadingly engage threads 312 of screw 300. Second end 170 preferably includes one or more apertures 173, which are arranged to accept residual bone material into hollow body 160, and central aperture 175.

Residual bone material is often produced when preparing proximate bone elements for the implantation of inter-bone implant 150 therebetween, as described in detail infra. The residual bone material often contains viable osteocytes, which can help rebuild bony matrix and enable the proximate bone elements to form a bony union therebetween and, ultimately, fuse. Implant 150 may also include bone morphogenic proteins, such as BMP-2 and BMP-7, which serve to induce such bony union. Outer surface 161 of body portion 160 is preferably irregular and includes at least one, but preferably a plurality, of apertures 165. The irregularity of outer surface 161 may be in the form of protuberances, for example, threads 163 as shown in the figures. The irregularity of outer surface 161 helps secure implant 150 between proximate bone elements by creating a frictional engagement between implant 150 and the bone elements. Apertures 165 are also arranged to receive residual bone material into body 160.

Clamp 200 comprises: base 210, which is preferably in the form of a substantially planar plate, and includes eyelet 215 operatively arranged to receive shaft 310 therethrough; and, a pair of opposed jaws, 240 and 270, pivotally connected to base 210. Jaws 240 and 270 may comprise any number of teeth, the shape and structure of which may be adapted for particular bone elements, such as, a superior articular process and an inferior articular process of a facet joint. Additionally, clamp 200 may comprise more than the two jaws shown and described herein, and may also comprise as few as one pivotally connected jaw. Regardless of the particular adaptation, the teeth of the jaws comprise substantially opposed surfaces, between which at least a portion of each of the proximate bone elements is immovably secured, as described in further detail infra.

In the particular embodiment shown and described herein, jaw 240 preferably comprises two teeth, namely, first tooth 250 and second tooth 260. First tooth 250 comprises first inner surface 254 and terminates at first pointed tip 252. Second tooth 260 comprises second inner surface 264 and terminates second pointed tip 262. First and second pointed tips 252 and 262, respectively, are arranged to frictionally engage and/or pierce the surface of the proximate bone elements.

Likewise, jaw 270 preferably comprises two teeth, namely, third tooth 280 and fourth tooth 290. Third tooth 280 comprises third inner surface 284 and terminates at third pointed tip 282. Fourth tooth 290 comprises fourth inner surface 294 and terminates fourth pointed tip 292. Third and fourth pointed tips 282 and 292, respectively, are arranged to frictionally engage and/or pierce the surface of the proximate bone elements.

Jaws 240 and 270 may be pivotally connected to base 210 by any means known in the art. In the particular embodiment shown and described herein, base 210 includes barrels 212a and 212b. Barrel 212a is operatively arranged to fit between, and align with, barrels 241 and 243 of jaw 240, and pivot pin 267 is operatively arranged to extend through barrels 241, 212a, and 243. Together, barrels 241, 212a, 243, and pivot pin 267 form a hinge bearing which provides a pivotable connection between jaw 240 and base 210. Pivot pin 267 may include cap 269 affixed to one end to prevent it from sliding out of the barrels.

Likewise, barrel 212b is operatively arranged to fit between, and align with, barrels 271 and 273 of jaw 270, and pivot pin 297 is operatively arranged to extend through barrels 271, 212b, and 273. Together, barrels 271, 212b, 273, and pivot pin 297 form a hinge bearing which provides a pivotable connection between jaw 270 and base 210. Pivot pin 297 may include cap 299 affixed to one end to prevent it from sliding out of the barrels.

Jaw 240 is arranged substantially opposed to jaw 270, such that first and second inner surfaces 254 and 264, respectively, of jaw 240 are arranged substantially opposed to third and fourth inner surfaces 284 and 294, respectively, of jaw 270, thereby defining mouth 230. It is between these opposed surfaces that at least a portion of each of the proximate bone elements is immovably secured, as described in further detail infra. Jaws 240 and 270 are also arranged to pivot toward and/or away from each other.

In a preferred embodiment, jaws 240 and 270 further comprise actuators 245 and 275, respectively. Jaw 240 is operatively arranged to pivot toward jaw 270 when a force is applied to actuator 245. Likewise, jaw 270 is operatively arranged to pivot toward jaw 240 when a force is applied to actuator 275. In one embodiment, head 320 is operatively arranged to apply mechanical force to actuator 245 and/or actuator 275 as head 320 moves toward base 210. In a further embodiment, head 320 applies such mechanical force simultaneously to actuators 245 and 275, thereby causing each actuator to simultaneously pivot toward each other.

In a preferred embodiment, device 100 includes plate 220, which is arranged between head 320 and base 210. Plate 220 is operatively arranged to provide a mechanical connection between head 320 and actuators 245 and 275, i.e., head 320 is operatively arranged to apply mechanical force to plate 220, which, in turn, is operatively arranged to apply mechanical force to actuators 245 and 275, as head 320 moves toward base 210. Plate 220 preferably includes aperture 225, which is substantially aligned with eyelet 215 and internally threaded aperture 154, and is arranged to receive shaft 310 therethrough. As shown in the figures, plate 220 may be embodied as a simple washer.

Figure 8:
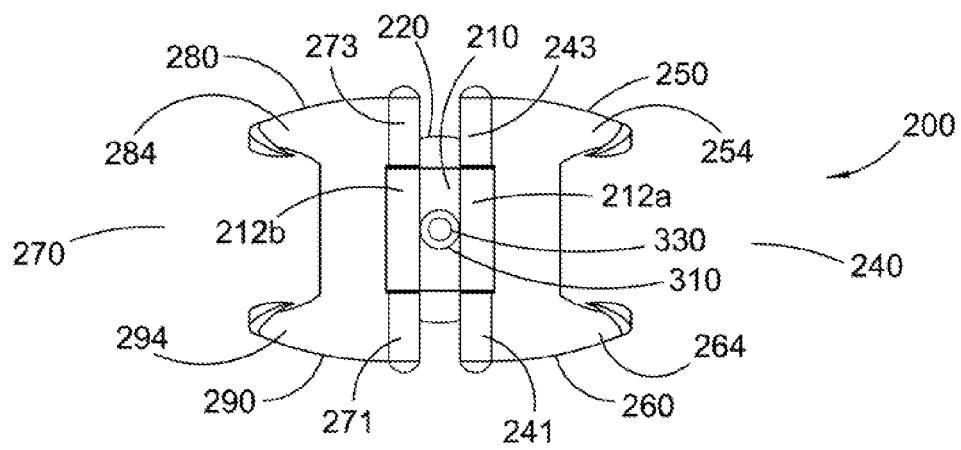
FIG. 8 is a bottom plan view the first embodiment bone fixation apparatus.
Figure 8A:
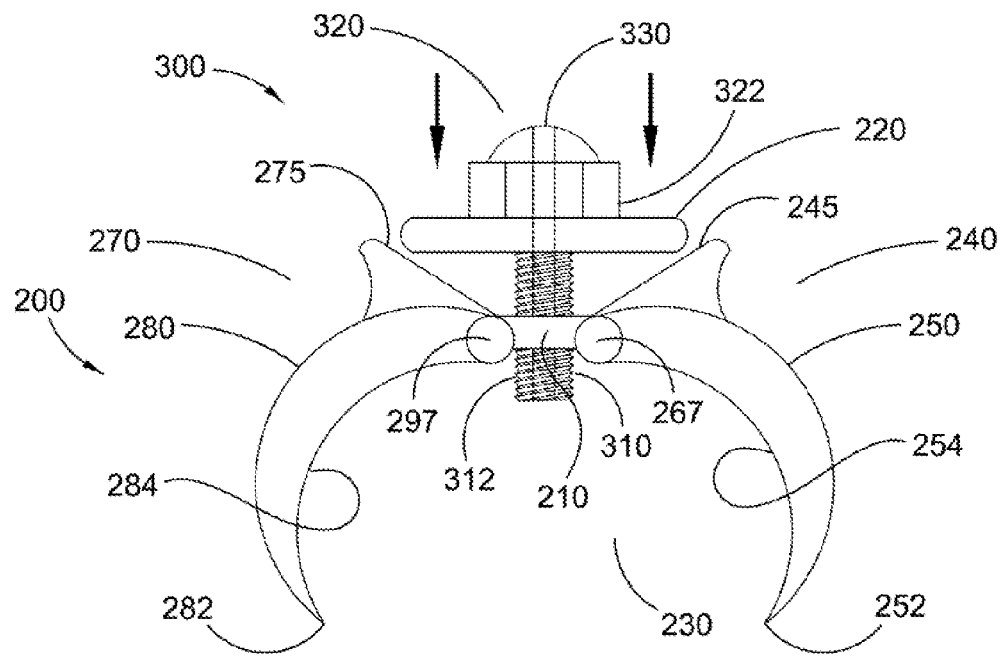
FIG. 8a is a side elevational view of a screw and the first embodiment bone fixation apparatus illustrating the screw moving downwardly.
Figure 8B:
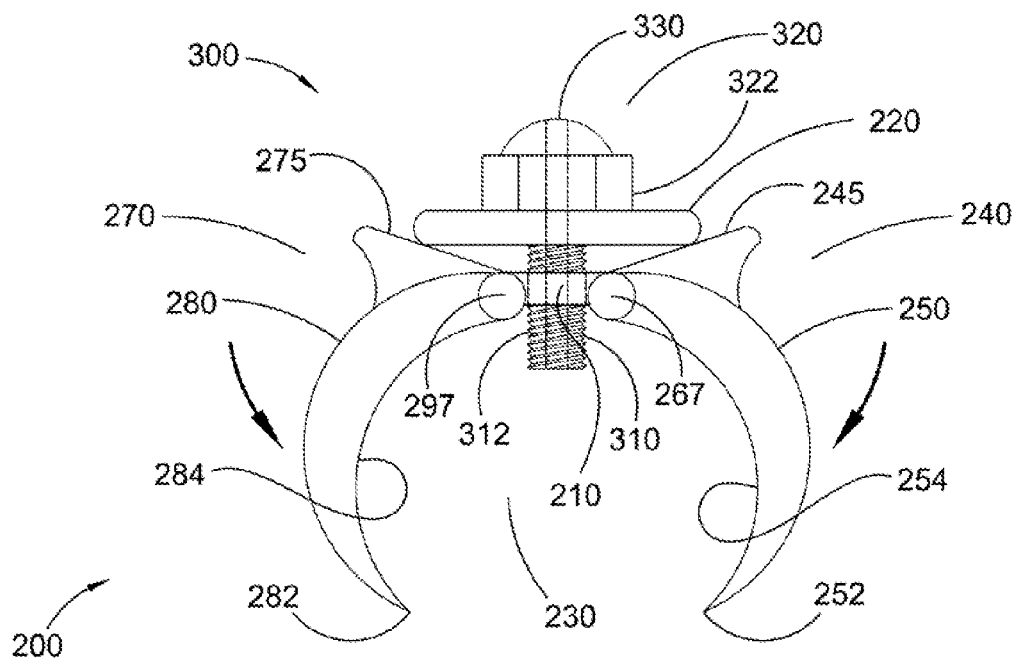
FIG. 8b is a side elevational view of the screw and bone fixation apparatus shown in FIG. 8a illustrating the actuation of the bone fixation apparatus by the screw.

The arrows in FIG. 8a illustrate head 320 moving toward base 210 in order to apply mechanical force to plate 220, and the arrows in FIG. 8b illustrate the pivoting of jaws 240 and 270 pivoting toward each other in response to the application of mechanical force on actuators 245 and 275 by plate 220.

Broadly, FIGS. 9a-9g illustrate the preferred method or procedure by which device 100 is implemented. Particularly: FIGS. 9a-9c illustrate the method by which proximate bone elements 80 and 90 are suitably prepared for the implementation of device 100; FIGS. 9d-9e illustrate the method by which inter-bone implant 150 is implanted between the suitably prepared proximate bone elements 80 and 90; and, FIGS. 9f-9g illustrate the method by which the bone fixation apparatus, specifically, clamp 200, is arranged to mechanically fix the positions of proximate bone elements 80 and 90 relative to each other, and the method by which screw 300 is operatively arranged to secure clamp 200 to inter-bone implant 150.

As shown in FIG. 9a, the initial step in the procedure includes inserting a Kirschner wire, hereinafter referred to as K-wire 30, between proximate bone elements 80 and 90. K-wire 30 is operatively arranged to guide the tools involved in suitably preparing proximate bone elements 80 and 90, as well as, the various components of device 100, toward proximate bone elements 80 and 90. FIG. 9b illustrates the second step in the procedure wherein first drill 40 is guided by K-wire 30 toward bone elements 80 and 90, as indicated by the arrows. First drill 40 is preferably hollow so that K-wire 30 can be arranged in its interior, in order to guide it toward proximate bone elements 80 and 90. Additionally, first drill 40 may include suction channel 41, which is operatively arranged to remove excess bone material created by the drilling process, as is illustrated by the arrows proximate to channel 41 in FIGS. 9b and 9c. FIG. 9c illustrates the third step in the procedure wherein first drill 40 removes bone material from both proximate bone elements 80 and 90.

As shown in FIG. 9d, first drill 40 is operatively arranged to remove bone material from bone elements 80 and 90, thereby generating cavity 85, which is defined by bone elements 80 and 90. Cavity 85 is arranged to receive inter-bone implant 150 therein. FIG. 9d illustrates the fourth step in the procedure wherein inter-bone implant 150 is guided by K-wire 30 toward cavity 85. Since implant 150 includes apertures 154 and 175 at opposite ends, and body portion 160 is preferably hollow, K-wire 30 can be arranged inside implant 150 in order to guide it toward cavity 85, as indicated by the arrows in FIG. 9d.

FIG. 9e illustrates the fifth step in the procedure wherein implant 150 is arranged between suitably prepared bone elements 80 and 90. Implant 150 is preferably arranged such that outer surface 161 is in contact with proximate bone elements 80 and 90, particularly by means of a frictional engagement of threads 163 with bone elements 80 and 90, thereby mitigating any movement of implant 150 within cavity 85.

Clamp 200 and screw 300 are arranged to be guided by K-wire 30 toward implant 150 and proximate bone elements 80 and 90. Particularly, K-wire 30 can be threaded through eyelet 215 in order to guide clamp 200 toward implant 150 and proximate bone elements 80 and 90. In a preferred embodiment, screw 300 includes through-bore 330, through which K-wire 30 can be threaded in order to guide screw 300 toward eyelet 215 and internally threaded aperture 154.

FIG. 9f illustrates the sixth step in the procedure wherein shaft 310 is arranged through eyelet 215 and is threadingly engaging internally threaded aperture 154, as illustrated by the semicircular arrow around K-wire 30. As threads 312 of shaft 310 positively engage internally threaded aperture 154, head 320 is drawn toward base 210 and applies mechanical force to plate 220. Plate 220, in turn, applies mechanical force to actuators 245 and 275, which cause jaws 240 and 270 to pivot toward each other, as illustrated by the arrows proximate the jaws.

FIG. 9g illustrates the seventh, and relatively final, step in the procedure wherein inter-bone implant 150 is arranged between suitably prepared proximate bone elements 80 and 90; clamp 200, is fixing the positions of proximate bone elements 80 and 90 relative to each other by immovably securing at least a portion of bone elements 80 and 90 between substantially opposed surfaces 254 and 284, eyelet 215 is substantially aligned with internally threaded aperture 154, and screw 300 is securing clamp 200 to inter-bone implant 150.

Figure 10:
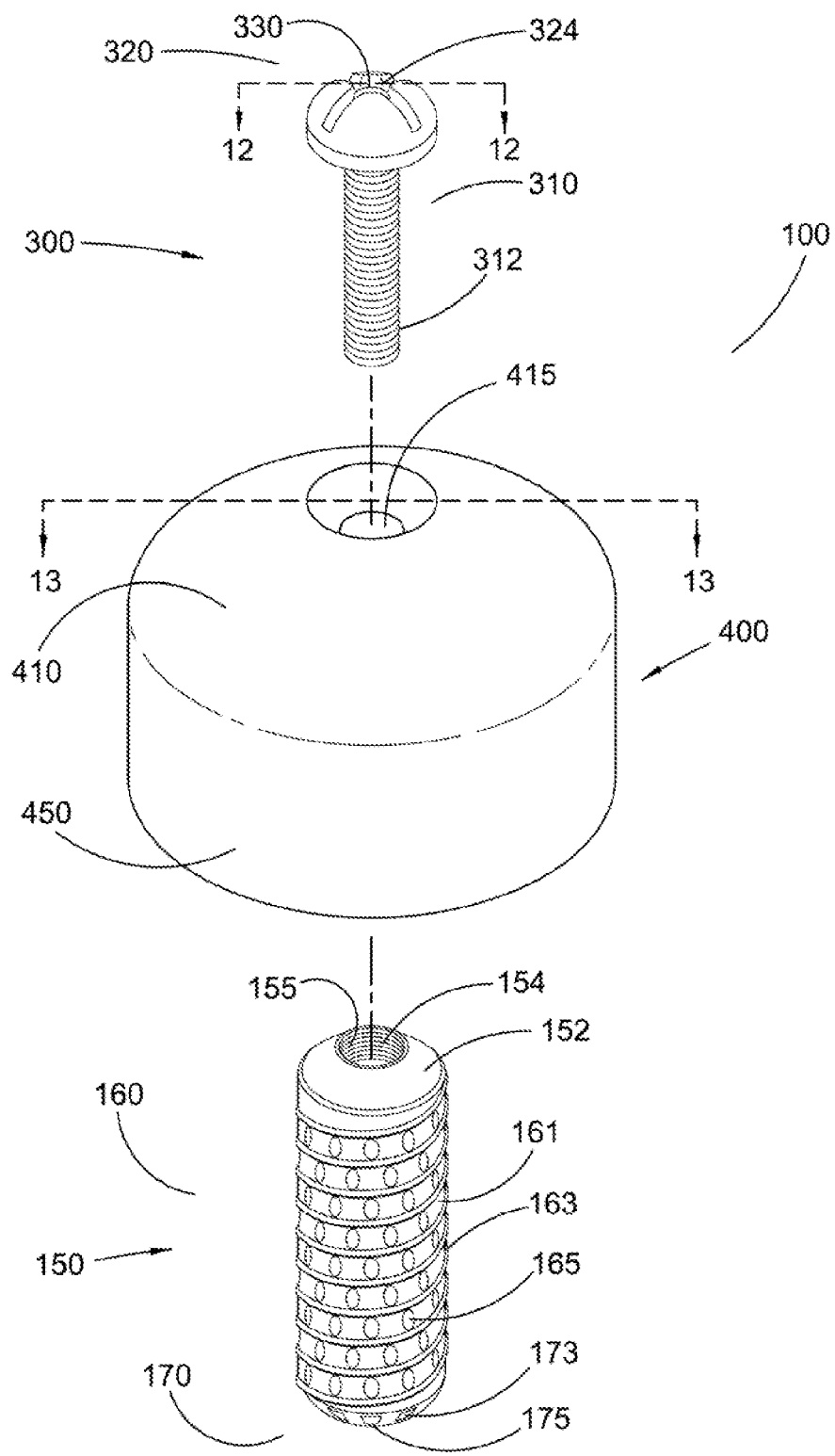
FIG. 10 is an exploded perspective view of a second embodiment of the present invention facet fixation device.

The second embodiment facet fixation device 100, is best understood in view of FIGS. 10-14h. FIG. 10 is a perspective view of device 100 broadly comprising inter-bone implant 150, screw 300, and bone fixation apparatus 400, hereinafter referred to as cap 400.

Screw 300, which may be any suitable screw, broadly includes head 320, shaft 310 having threads 312, and, preferably, through-bore 330, as shown in FIGS. 11 and 12. The screw drive of screw 300 may be of any type, but is preferably cruciform screw drive 324 when used in combination with cap 400.

As in the first embodiment, inter-bone implant 150 includes body 160, which is preferably hollow and either cylindrical or frustoconical, first end 152, and second end 170. First end 152 includes aperture 154 having internal threads 155, which are operatively arranged to threadingly engage threads 312 of screw 300. Second end 170 preferably includes one or more apertures 173, which are arranged to accept residual bone material into hollow body 160, and central aperture 175. Outer surface 161 of body portion 160 is preferably irregular and includes at least one, but preferably a plurality, of apertures 165. The irregularity of outer surface 161 may be in the form of protuberances, for example, threads 163 as shown in the figures. The irregularity of outer surface 161 helps secure implant 150 between proximate bone elements by creating a frictional engagement between implant 150 and the bone elements. Apertures 165 are also arranged to receive residual bone material into body 160.

Cap 400 comprises: base 410, which is preferably in the form of a substantially arcuate plate, and includes eyelet 415 operatively arranged to receive shaft 310 therethrough; and, annular wall 450 extending from base 410, which, in conjunction with base 410, defines inner chamber 430. Eyelet 415 is preferably recessed so that head 320 fits substantially flush with the surface of base 410 when assembled together Annular wall 450 may be a cylindrical form, as shown and described, but may also be adapted for different proximate bone elements, the particular structure of which may necessitate a different shape for annular wall 450, such as, a frustoconical form.

Regardless of the particular adaptation, annular wall 450 comprises inner annular surface 452, which preferably includes threads 453, as shown in FIG. 13. Inner annular surface 452 provides a continuum of substantially opposed surfaces, since any location on inner annular surface 452 has a complimentary location, diametrically opposed across chamber 430, on surface 452. Thus, inner annular surface 452 provides a continuum of diametrically opposed surfaces, between which at least a portion of each of the proximate bone elements is immovably secured, as described in further detail infra.

Figure 14F:
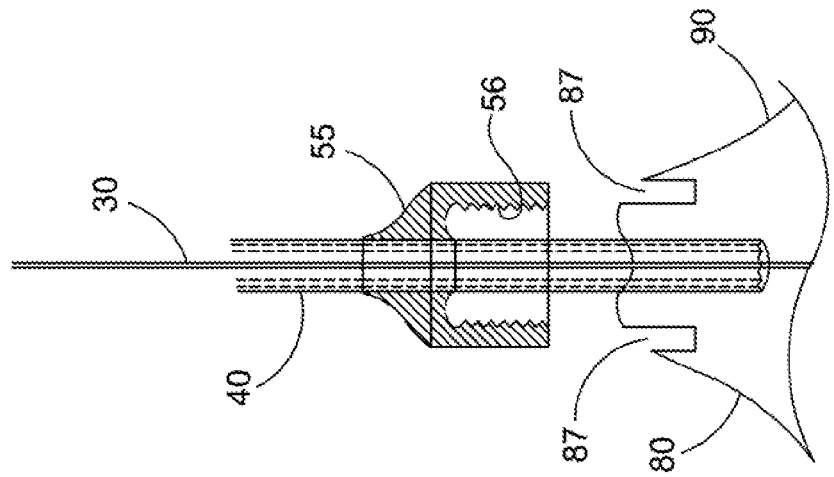
FIG. 14f is a side view showing a sixth step in the implementation of the second embodiment facet fixation device.
Figure 14E:
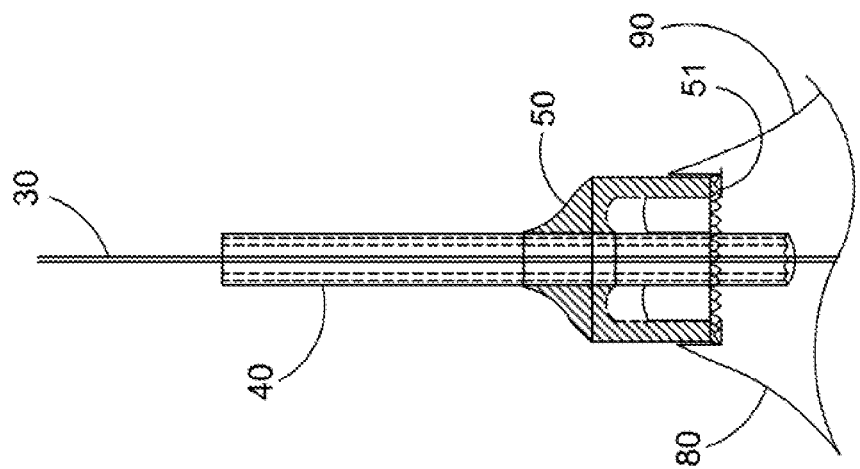
FIG. 14e is a side view showing a fifth step in the implementation of the second embodiment facet fixation device.
Figure 14D:
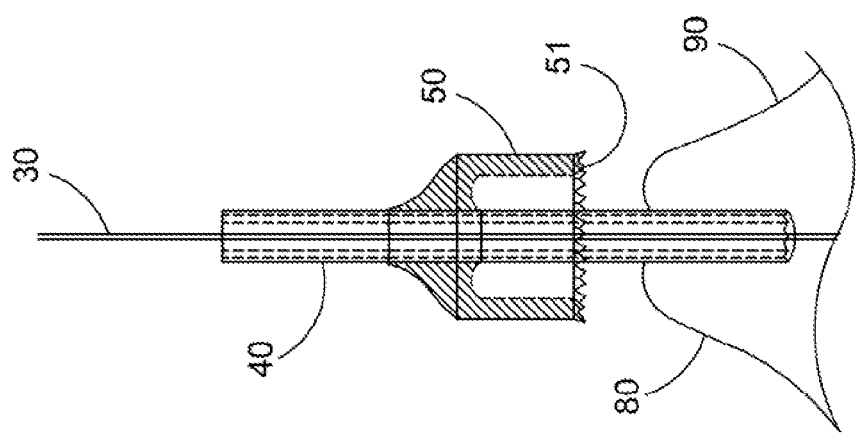
FIG. 14d is a side view showing a fourth step in the implementation of the second embodiment facet fixation device.
Figure 14H:
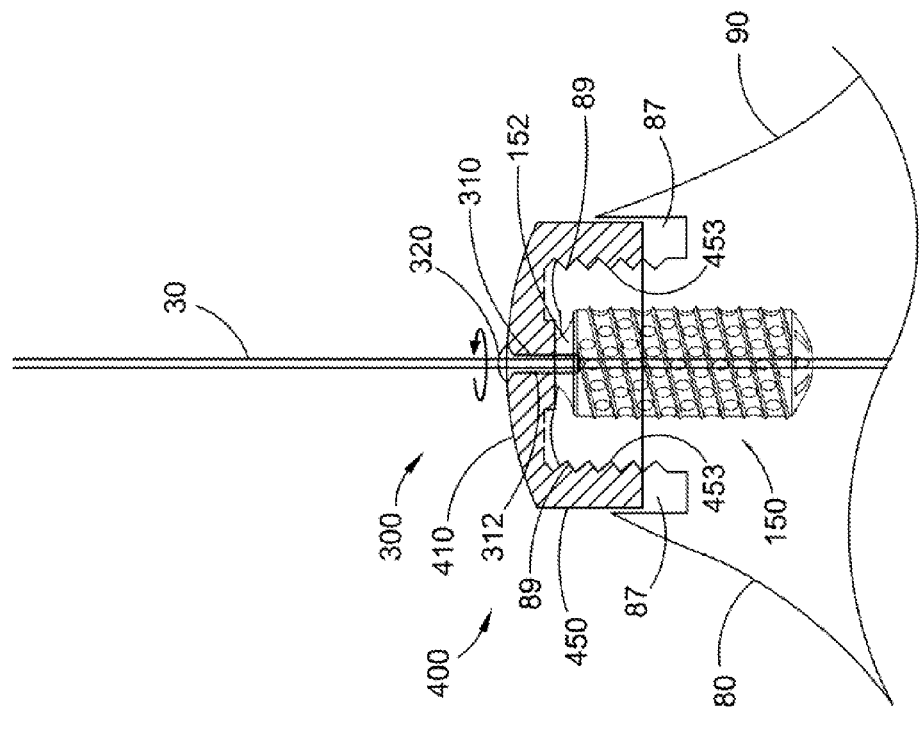
FIG. 14h is a side view showing an eighth step in the implementation of the second embodiment facet fixation device for the fixation of proximate bone elements.
Figure 14G:
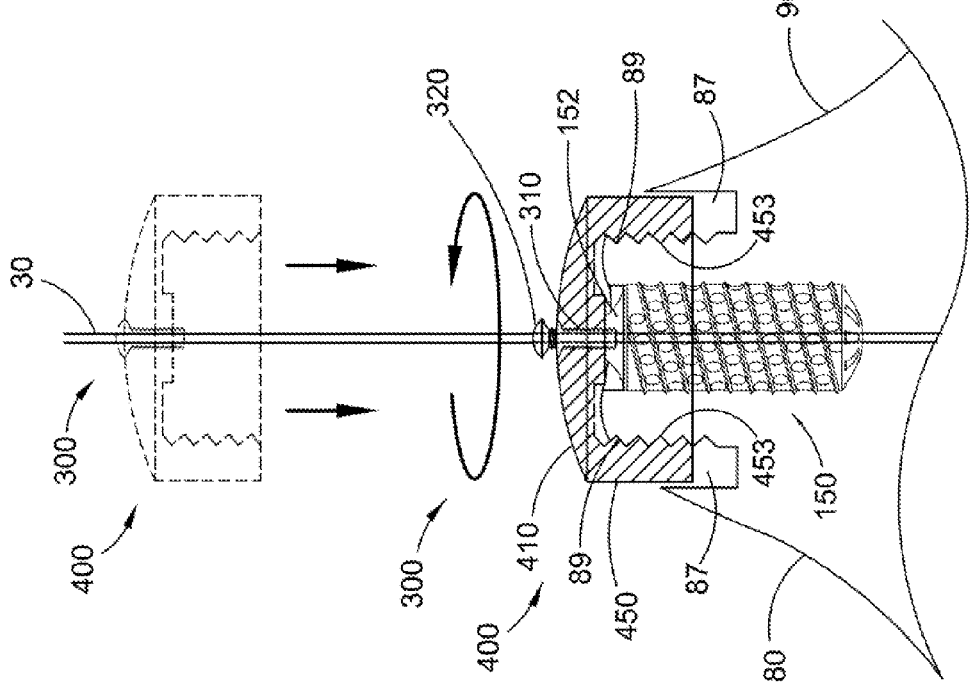
FIG. 14g is a side view showing a seventh step in the implementation of the second embodiment facet fixation device.

Broadly, FIGS. 14*a*-14*h* illustrate the preferred method or procedure by which device 100 is implemented. Particularly: FIGS. 14*a*-14*f* illustrate the method by which proximate bone elements 80 and 90 are suitably prepared for the implementation of device 100; FIGS. 14*g*-14*h* illustrate the method by which the bone fixation apparatus, namely, cap 400, is arranged to mechanically fix the positions of proximate bone elements 80 and 90 relative to each other, and the method by which screw 300 is operatively arranged to secure cap 400 to inter-bone implant 150. The method by which inter-bone implant 150 is implanted between the suitably prepared proximate bone elements 80 and 90 is not shown in these figures as it is substantially identical to steps described supra and shown in FIGS. 9*d*-9*e*.

The first three steps for suitably preparing proximate bone elements 80 and 90 are illustrated in FIGS. 14*a*-14*c*, and are substantially identical to the first three respective steps for implementing the first embodiment, as described supra and shown in FIGS. 9*a*-9*c*. Particularly, FIG. 14*a* shows the initial step wherein K-wire 30 is inserted between proximate bone elements 80 and 90. K-wire 30 is operatively arranged to guide the tools involved in suitably preparing proximate bone elements 80 and 90, as well as, the various components of device 100, toward proximate bone elements 80 and 90. FIG. 14*b* illustrates the second step in the procedure wherein first drill 40 is guided by K-wire 30 toward bone elements 80 and 90, as indicated by the arrows. First drill 40 is preferably hollow so that K-wire 30 can be arranged in its interior, in order to guide it toward proximate bone elements 80 and 90. Additionally, first drill 40 may include suction channel 41, which is operatively arranged to remove excess bone material created by the drilling process, as is illustrated by the arrows proximate to channel 41 in FIGS. 14*b* and 14*c*. FIG. 14*c* illustrates the third step in the procedure wherein first drill 40 removes bone material from both proximate bone elements 80 and 90, thereby generating cavity 85.

To suitably prepare proximate bone elements 80 and 90 for the implantation of second embodiment device 100, the additional steps shown in FIGS. 14*d*-14*f* are required. FIG. 14*d* illustrates a fourth step wherein second drill 50 is guided by K-wire 30 toward proximate bone elements 80 and 90. Second drill 50 comprises an annular wall having a ring of teeth 51 along its circular leading edge. As shown in FIGS. 14*e* and 14*f*, second drill 50 is operatively arranged to carve annular recess 87 into bone elements 80 and 90.

FIG. 14*f* shows the next step wherein third drill 55 is guided by K-wire 30 toward proximate bone elements 80 and 90, particularly toward annular recess 87. Third drill 55 is a threading tool comprising an annular wall having threaded inner annular surface 56, which is operatively arranged to carve threads 89 into bone elements 80 and 90 within annular recess 87, as shown in FIGS. 14*g* and 14*h* Annular recess 87 is arranged to fittingly receive annular wall 450 of cap 400. Additionally, 89 threads are operatively arranged to threadingly engage threads 453 of inner annular surface 452.

FIGS. 14*g*-14*h* show inter-bone implant 150 already implanted between proximate bone elements 80 and 90 within cavity 85. Cap 400 and screw 300 are arranged to be guided by K-wire 30 toward implant 150 and proximate bone elements 80 and 90, as illustrated with the parallel arrows shown in FIG. 14*g*. Particularly, K-wire 30 can be threaded through eyelet 415 in order to guide cap 400 toward implant 150 and proximate bone elements 80 and 90, as shown in FIG. 14*g*. In a preferred embodiment, screw 300 includes throughbore 330, through which K-wire 30 can be threaded in order to guide screw 300 toward eyelet 415 and internally threaded aperture 154.

FIG. 14*g* further illustrates how threads 453 of inner annular surface 452 threadingly engage threads 89 of annular recess 87, as indicated by the large semicircular arrow around K-wire 30. As threads 453 threadingly engage threads 89, proximate bone elements 80 and 90 are immovably secured between the continuum of substantially opposed surfaces provided by inner annular surface 452, as described supra.

FIG. 14*h* illustrates the relatively final step in the procedure wherein shaft 310 is arranged through eyelet 415 and is threadingly engaging internally threaded aperture 154, as indicated by the small semicircular arrow around K-wire 30. As threads 312 of shaft 310 positively engage internally threaded aperture 154, head 320 is drawn toward base 410 until cap 400 is secured to inter-bone implant 150.

FIGS. 15*a*-15*j* illustrate an alternate preferred method or procedure by which device 100 is implemented. Person of skill in the art will recognize that the choice of method would depend on the individual circumstances of each surgical situation. Particularly, FIGS. 15*a*-15*f* illustrate the method by which proximate bone elements 80 and 90 are suitably prepared for the implantation of implant 150. FIGS. 15*g*-15*j* illustrate the method by which the bone fixation apparatus, namely, cap 500, is arranged to fix the positions of proximate bone elements 80 and 90 relative to each other and the method by which cap 500 is attached to inter-bone implant 150.

Figure 15A:
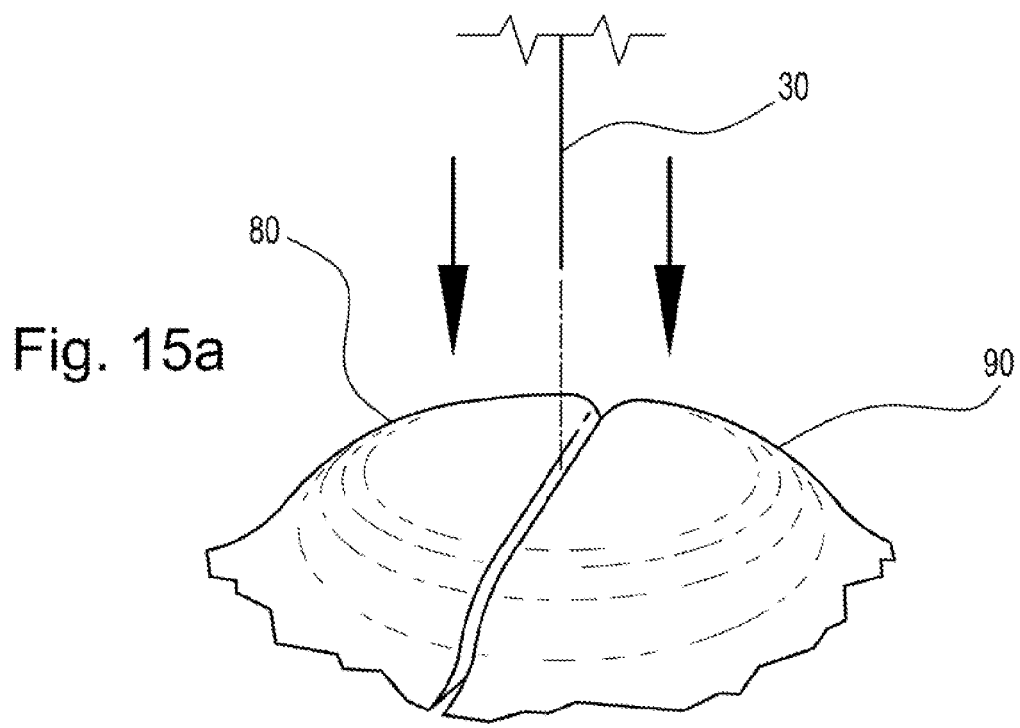
FIG. 15a is a side perspective view showing a first step in the implementation of the third embodiment facet fixation device.
Figure 15B:
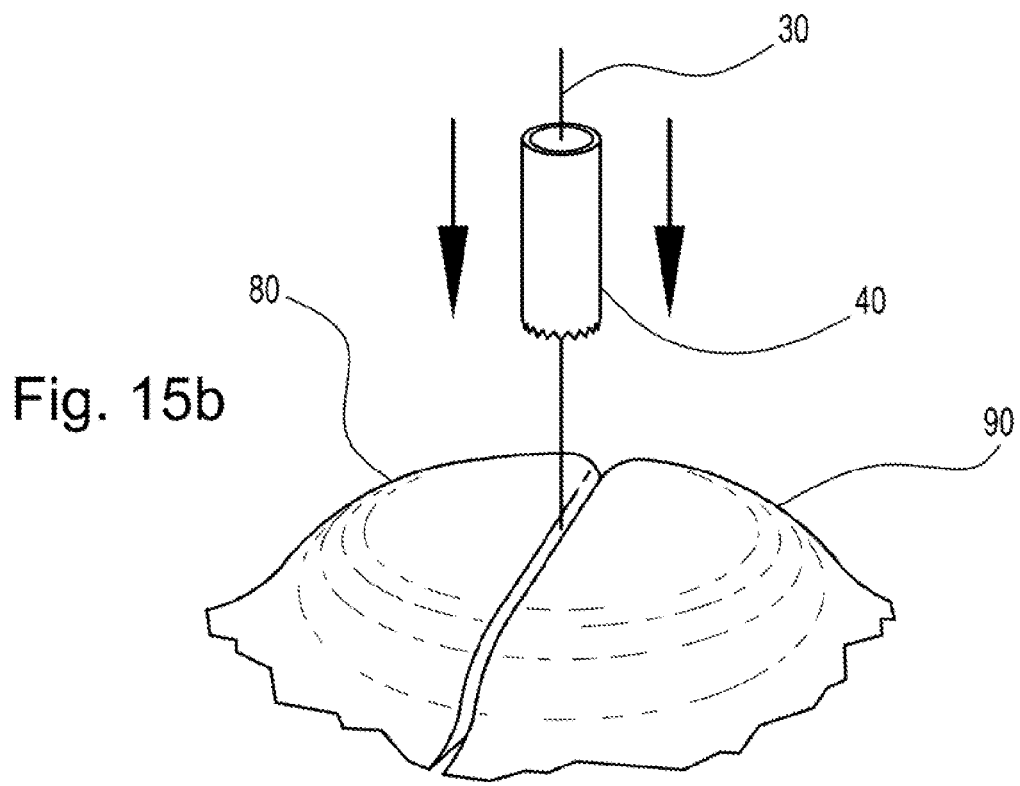
FIG. 15b is a side perspective view showing a second step in the implementation of the third embodiment facet fixation device.

The first three steps for suitably preparing proximate bone elements 80 and 90 are illustrated in FIGS. 15*a*-15*d*, and are substantially identical to the first three respective steps for implementing the first embodiment, as described supra and shown in FIGS. 9*a*-9*c*. Particularly, FIG. 15*a* shows the preferred initial step wherein K-wire 30 is inserted between proximate bone elements 80 and 90. K-wire 30 is operatively arranged to guide the tools involved in suitably preparing proximate bone elements 80 and 90, as well as the fixation device 500 described below, toward proximate bone elements 80 and 90. FIG. 15*b* illustrates the second step in the procedure wherein first drill 40 is guided by K-wire 30 toward bone elements 80 and 90, as indicated by the arrows. First drill 40 is preferably hollow so that K-wire 30 can be arranged in its interior, in order to guide it toward proximate bone elements 80 and 90. Additionally, first drill 40 may include suction channel 41, seen in FIG. 9*c*, which is operatively arranged to remove excess bone material created by the drilling process, as is illustrated by the arrows proximate to channel 41 in FIG. 9*c*. FIG. 15*c* illustrates the third step in the procedure wherein first drill 40 removes bone material from both proximate bone elements 80 and 90, thereby generating cavity 85. FIG. 15*d* shows the cavity 85 prepared for implant 150 by first drill 40 after drilling is completed.

Figure 15E:
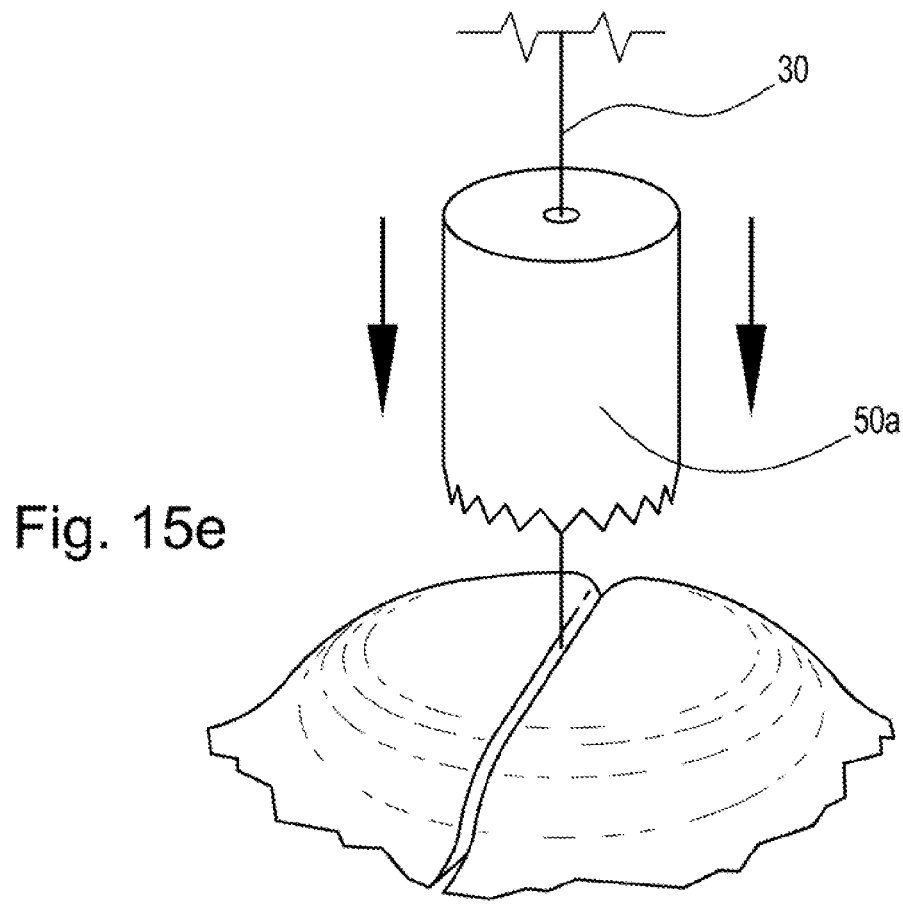
FIG. 15e is a side perspective view illustrating a fourth step wherein a fluted flat bottom end mill is moved toward the proximate bone elements.
Figure 15F:
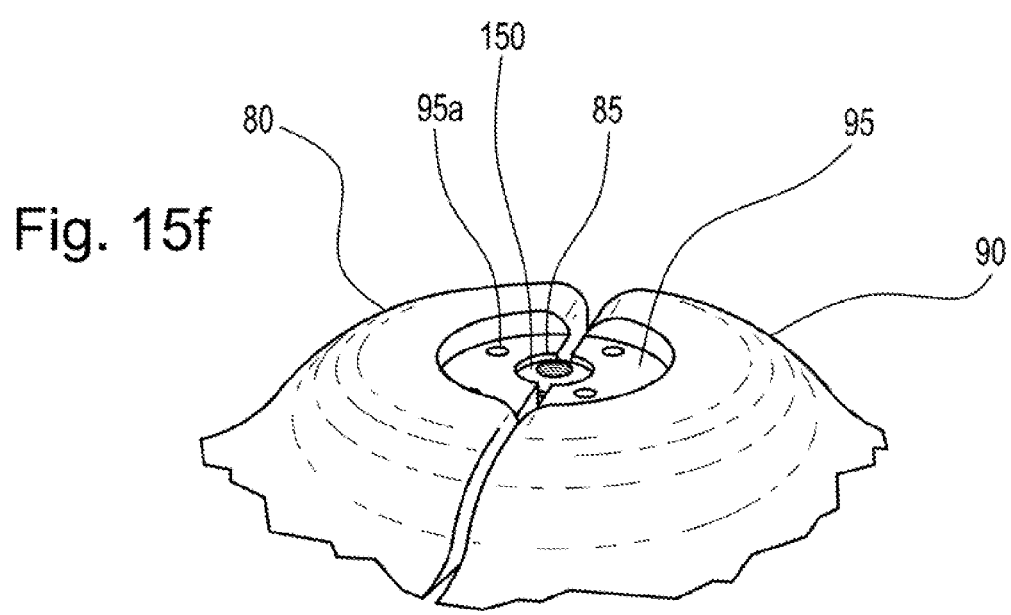
FIG. 15f is a side perspective view showing drilled pilot holes in the recess formed by the flat bottom end mill and the interbone implant positioned in the bore between the proximate bone elements.
Figure 15G:
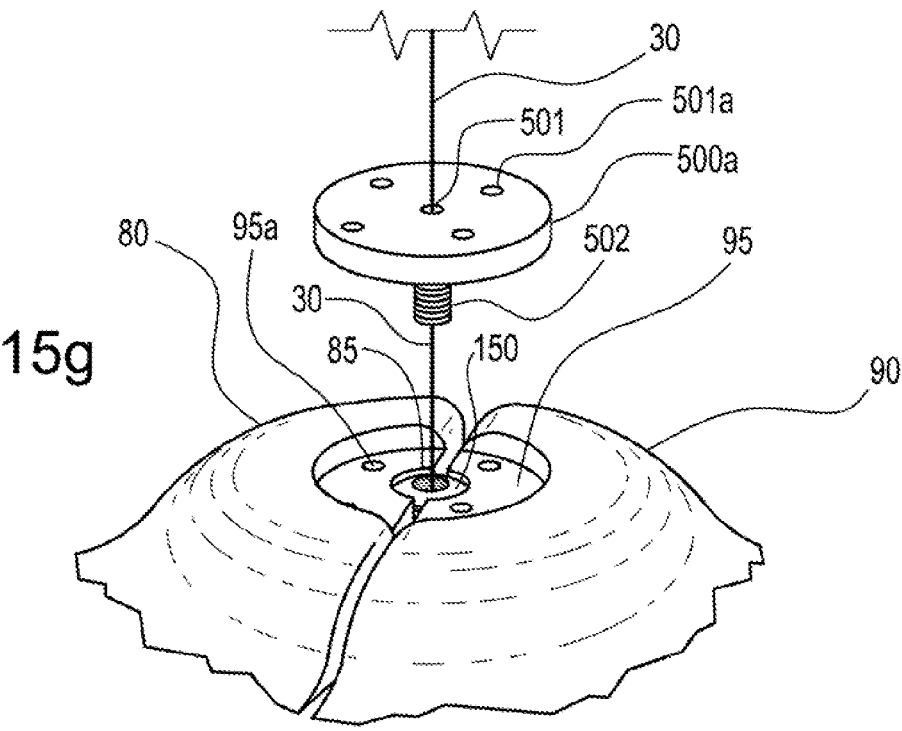
FIG. 15g is a side perspective exploded view depicting the suitably prepared recess with pilot holes with one embodiment of the fixation cap in the form of a circular cap screw.

To suitably prepare proximate bone elements 80 and 90 for the implantation of implant 150 and the third embodiment of the fixation device, screw cap 500, the additional steps shown in FIGS. 15*e*-15*f* are required. FIGS. 15*g* and 15*i* show two forms of screw cap 500, circular screw cap 500a ("cap 500a") and cross or x-shaped screw cap 500b ("cap 500b") (collectively "cap 500"), respectively. Cap 500a includes a circular cap with a hollow externally threaded stem 502 and, preferably, central bore 501 that extends continuously through both the circular cap and hollow stem 502 to form a cap screw. Preferably, cap 500 also includes screw holes 501a to accommodate screws 504 which are used to attach cap 500 to the bottom of recess 95. Stem 502 is threaded to threadably attach cap 500a to previously positioned implant 150 which has an internally threaded aperture 154 as described above.

FIG. 15e illustrates a fourth step wherein drill 50a, preferably guided by K-wire 30 is moved toward proximate bone elements 80 and 90. Third drill 50a is a flat bottom end mill having a flat bottom with flutes to bore a common recess 95 between proximate bone elements 80 and 90. By common is meant that recess 95 spans each of the proximate bone elements, in this example proximate bone elements 80 and 90. Within recess 95, a pilot drill is used to drill at least one pilot hole 95a into each proximate bone element 80 and 90. FIG. 15f shows the completed recess 95 with pilot holes 95a. Pilot holes are holes with a diameter smaller than a screw that will be threaded into the pilot hole in order to allow the threading to be more easily started.

FIG. 15g is a side perspective view depicting the suitably prepared recess 95 with pilot holes 95a along with circular cap 500a. Similarly, FIG. 15i shows an x-shaped cap 500b in an exploded view over recess 95 and pilot holes 95a. Caps 500a and 500b each include at least one cap hole 501a aligned with at least one pilot hole 95a in each of proximate bone elements 80 and 90. Center hole 501 is in the center of cap 500a and at the center of the junction of the legs of cap 500b. Center hole 501 allows the use of K-wire 30 to guide the placement of cap 500a or 500b into recess 95 to be threaded into implant 150. Persons of skill in the art will recognize that caps having different shapes may also be effectively used. Also seen is implant 150 inserted into hole 85.

Figure 15H:
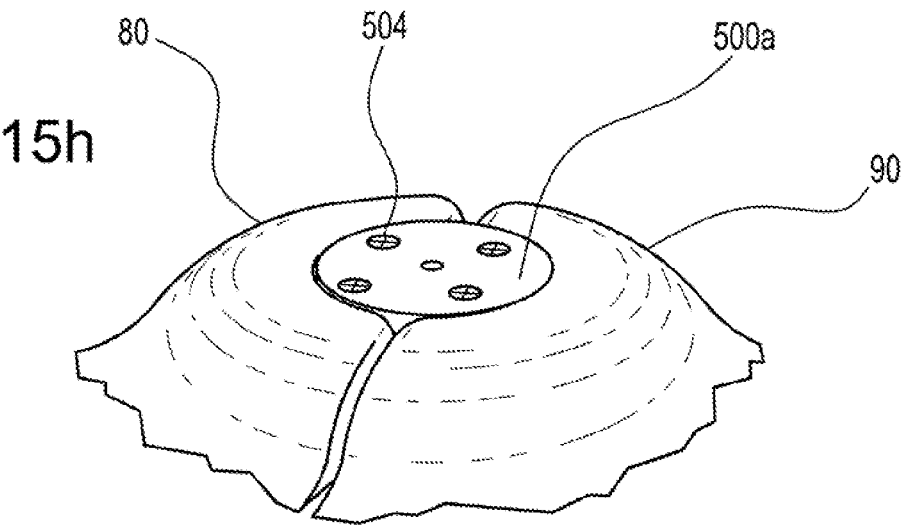
FIG. 15h is a side perspective view showing the circular cap screw fastened in place in the recess between the proximate bone elements.
Figure 15I:
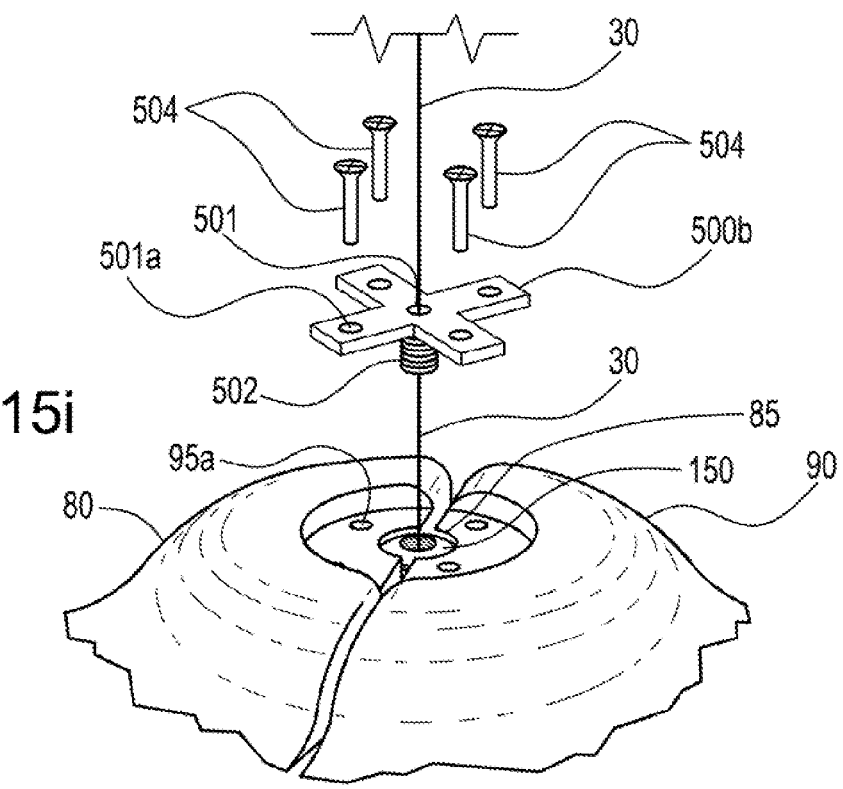
FIG. 15i is a side perspective exploded view depicting the suitably prepared recess with pilot holes with a second embodiment of the fixation cap in the form of a cross or x-shaped cap screw; and, FIG. 15j is a side perspective exploded view depicting the circular cap screwed in place in recess 95.
Figure 15J:
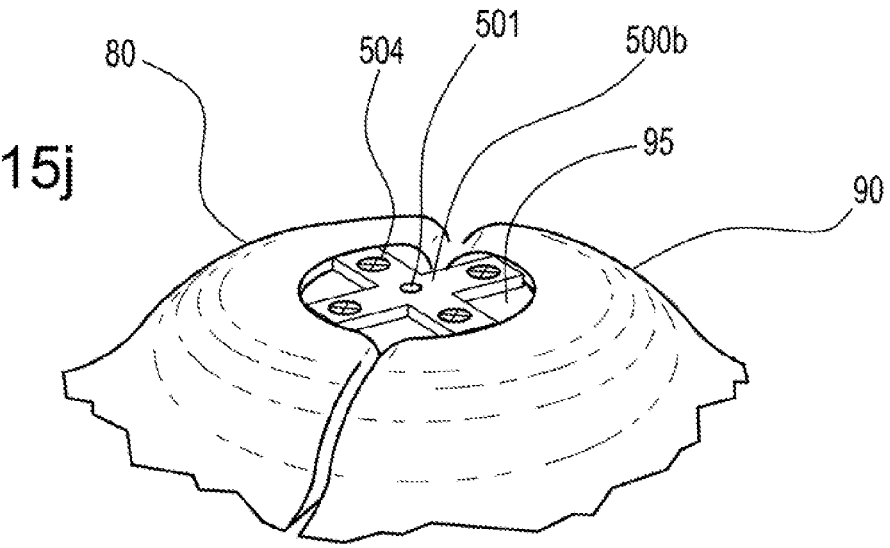
FIG. 15c is a side perspective view showing a third step in the implementation of the third embodiment facet fixation device.
FIG. 15d is a side perspective view showing the hole prepared for the implant after drilling is completed.

FIG. 15h shows cap 500a screwed in place in recess 95, while FIG. 15j depicts cap 500b screwed in place in recess 95. It can be seen that by threading screws 504 through cap holes 501a into pilot holes 95a, proximate bone elements 80 and 90 are kept in a fixed position relative to each other allowing proximate bone elements 80 and 90 to fuse to each other through implant 85.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

I claim:

1. A device for fixing the positions of proximate bone elements comprising:
   an interbone implant adapted to be implanted between suitably prepared proximate bone elements and including an internally threaded bore;
   a bone fixation apparatus comprising at least one hole wherein said bone fixation apparatus includes a cap sized to fit in a single recess common to each of said proximate bone elements, said cap having a plurality of cap holes extending through said cap and a threaded stem sized to threadably attach to said internally threaded bore to form a second threadable attachment;
   at least one screw inserted through said at least one hole and threadably attached to at least one of said proximate bone elements to form a first threadable attachment; and,
   wherein each of said proximate bone elements includes at least one pilot hole.

2. The device for fixing the positions of proximate bone elements as recited in claim 1 wherein said cap is a circular cap.

3. The device for fixing the positions of proximate bone elements as recited in claim 1 wherein said cap is an x-shaped cap.

4. The device for fixing the positions of proximate bone elements as recited in claim 1 wherein said at least one pilot hole is a plurality of pilot holes, and wherein at least one of said plurality of pilot holes is drilled into each of said bone elements, and wherein said first threadable attachment comprises each of said at least one screw threaded through at least one of said plurality of cap holes into one of said plurality of pilot holes.

5. The device for fixing the positions of proximate bone elements as recited in claim 1 wherein said interbone implant further comprises a body portion having an irregular outer surface.

6. The device for fixing the positions of proximate bone elements as recited in claim 1 wherein said bone fixation device further comprises a center hole.

\* \* \* \* \*